(12) United States Patent
McCambridge

(10) Patent No.: US 7,301,344 B2
(45) Date of Patent: Nov. 27, 2007

(54) Q-DAMPING CIRCUIT INCLUDING A HIGH TEMPERATURE SUPERCONDUCTOR COIL FOR DAMPING A HIGH TEMPERATURE SUPERCONDUCTOR SELF-RESONANT COIL IN A NUCLEAR QUADRUPOLE RESONANCE DETECTION SYSTEM

(75) Inventor: James D. McCambridge, Swarthmore, PA (US)

(73) Assignee: E.I. du Pont de Nemours & Co., Wilmington, DE (US)

( * ) Notice: Subject to any disclaimer, the term of this patent is extended or adjusted under 35 U.S.C. 154(b) by 0 days.

(21) Appl. No.: 10/994,783

(22) Filed: Nov. 22, 2004

(65) Prior Publication Data

US 2006/0082368 A1    Apr. 20, 2006

Related U.S. Application Data

(60) Provisional application No. 60/524,578, filed on Nov. 24, 2003.

(51) Int. Cl.
*G01V 3/00* (2006.01)

(52) U.S. Cl. .................................................. 324/322

(58) Field of Classification Search ................ 324/307, 324/309, 318, 322
See application file for complete search history.

(56) References Cited

U.S. PATENT DOCUMENTS

| | | | |
|---|---|---|---|
| 3,373,348 A | 3/1968 | Vanier et al. | |
| 3,764,892 A | 10/1973 | Rollwitz | |
| 4,027,768 A | 6/1977 | Riessen | |
| 4,072,768 A | 2/1978 | Fraser et al. | |
| 4,514,691 A | 4/1985 | De Los Santos et al. | |
| 5,036,279 A * | 7/1991 | Jonsen | 324/307 |
| 5,135,908 A | 8/1992 | Yang et al. | |
| 5,206,592 A * | 4/1993 | Buess et al. | 324/307 |
| 5,233,300 A | 8/1993 | Buess et al. | |
| 5,258,710 A | 11/1993 | Black et al. | |
| 5,262,394 A | 11/1993 | Wu et al. | |
| 5,276,398 A | 1/1994 | Withers et al. | |
| 5,351,007 A | 9/1994 | Withers et al. | |
| 5,418,213 A | 5/1995 | Tanaka et al. | |
| 5,457,385 A | 10/1995 | Sydney et al. | |
| 5,583,437 A | 12/1996 | Smith et al. | |
| 5,585,723 A * | 12/1996 | Withers | 324/318 |

(Continued)

FOREIGN PATENT DOCUMENTS

EP    0 426 851    5/1991

(Continued)

OTHER PUBLICATIONS

Garroway, et al., "Remote Sensing By Nuclear Quadrupole Resonance", IEEE Transactions on Geoscience and Remote Sensing, Jun. 2001, pp. 1108-1118, vol. 39, No. 6.

(Continued)

*Primary Examiner*—Dixomara Vargas
(74) *Attorney, Agent, or Firm*—George M. Medwick

(57) ABSTRACT

The use of a high temperature superconductor single loop or coil in the Q-damping circuit for a high temperature superconductor transmit, receive, or transmit and receive self-resonant coil in a nuclear quadrupole resonance system results in improved performance of the nuclear quadrupole resonance detection system.

8 Claims, 1 Drawing Sheet

U.S. PATENT DOCUMENTS

| | | |
|---|---|---|
| 5,592,083 A | 1/1997 | Magnuson et al. |
| 5,594,338 A | 1/1997 | Magnuson |
| 5,656,937 A | 8/1997 | Cantor |
| 5,661,400 A | 8/1997 | Plies et al. |
| 5,750,473 A | 5/1998 | Shen |
| 5,751,146 A | 5/1998 | Hrovat |
| 5,804,967 A | 9/1998 | Miller et al. |
| 5,814,987 A | 9/1998 | Smith et al. |
| 5,814,989 A | 9/1998 | Smith et al. |
| 5,814,992 A | 9/1998 | Busse-Gracitz et al. |
| 5,872,080 A | 2/1999 | Arendt et al. |
| 5,952,269 A | 9/1999 | Ma et al. |
| 5,973,495 A | 10/1999 | Mansfield |
| 5,986,455 A | 11/1999 | Magnuson |
| 5,999,000 A | 12/1999 | Srinivasan |
| 6,025,719 A | 2/2000 | Anderson |
| 6,054,856 A | 4/2000 | Garroway et al. |
| 6,088,423 A | 7/2000 | Krug et al. |
| 6,091,240 A | 7/2000 | Smith et al. |
| 6,104,190 A | 8/2000 | Buess et al. |
| 6,108,569 A | 8/2000 | Shen |
| 6,150,816 A | 11/2000 | Srinivasan |
| 6,166,541 A | 12/2000 | Smith et al. |
| 6,169,399 B1 | 1/2001 | Zhang et al. |
| 6,194,898 B1 | 2/2001 | Magnuson et al. |
| 6,201,392 B1 | 3/2001 | Anderson et al. |
| 6,218,943 B1 | 4/2001 | Ellenbogen |
| 6,242,918 B1 | 6/2001 | Miller et al. |
| 6,291,994 B1 * | 9/2001 | Kim et al. ................. 324/300 |
| 6,335,622 B1 | 1/2002 | James et al. |
| 6,370,404 B1 | 4/2002 | Shen |
| D459,245 S | 6/2002 | Power |
| 6,420,872 B1 | 7/2002 | Garroway et al. |
| 6,486,838 B1 | 11/2002 | Smith et al. |
| 6,538,445 B2 | 3/2003 | James et al. |
| 6,541,966 B1 | 4/2003 | Keene |
| 6,556,013 B2 * | 4/2003 | Withers ..................... 324/322 |
| 6,566,873 B1 | 5/2003 | Smith et al. |
| 6,590,394 B2 | 7/2003 | Wong et al. |
| 6,617,591 B1 | 9/2003 | Simonson et al. |
| 6,653,917 B2 | 11/2003 | Kang et al. |
| 6,751,489 B2 | 6/2004 | Shen |
| 6,751,847 B1 | 6/2004 | Brey et al. |
| 6,777,937 B1 | 8/2004 | Miller et al. |
| 6,819,109 B2 | 11/2004 | Sowers et al. |
| 6,822,444 B2 | 11/2004 | Lai |
| 6,847,208 B1 | 1/2005 | Crowley et al. |
| 6,952,163 B2 | 10/2005 | Muey et al. |
| 6,956,476 B2 | 10/2005 | Buess et al. |
| 6,958,608 B2 | 10/2005 | Takagi et al. |
| 7,049,814 B2 | 5/2006 | Mann |
| 7,106,058 B2 | 9/2006 | Wilker et al. |
| 2002/0068682 A1 | 6/2002 | Shen |
| 2002/0153891 A1 | 10/2002 | Smith et al. |
| 2002/0156362 A1 | 10/2002 | Bock et al. |
| 2002/0169374 A1 | 11/2002 | Jevtic |
| 2002/0190715 A1 | 12/2002 | Marek |
| 2003/0020553 A1 | 1/2003 | Gao et al. |
| 2003/0062886 A1 | 4/2003 | Wong et al. |
| 2003/0071619 A1 | 4/2003 | Sauer et al. |
| 2003/0119677 A1 | 6/2003 | Olyan et al. |
| 2003/0136920 A1 | 7/2003 | Flores et al. |
| 2004/0124840 A1 | 7/2004 | Reykowski |
| 2004/0222790 A1 | 11/2004 | Karmi et al. |
| 2004/0251902 A1 | 12/2004 | Takagl et al. |
| 2005/0104593 A1 | 5/2005 | Laubacher et al. |
| 2005/0122109 A1 * | 6/2005 | Wilker et al. ............... 324/318 |
| 2005/0140371 A1 * | 6/2005 | Alvarez ..................... 324/322 |
| 2005/0146331 A1 | 7/2005 | Flaxman et al. |
| 2005/0206382 A1 | 9/2005 | Laubacher et al. |
| 2005/0246345 A1 | 11/2005 | Alvarez |
| 2005/0258831 A1 | 11/2005 | Alvarez |
| 2005/0264289 A1 | 12/2005 | Alvarez |
| 2005/0270028 A1 | 12/2005 | Alvarez |
| 2006/0012371 A1 * | 1/2006 | Laubacher et al. ......... 324/322 |
| 2006/0038563 A1 | 2/2006 | Cisholm et al |
| 2006/0082368 A1 | 4/2006 | McCambridge |
| 2006/0119360 A1 | 6/2006 | Yamamoto et al. |

FOREIGN PATENT DOCUMENTS

| | | |
|---|---|---|
| EP | 1 122 550 A1 | 8/2001 |
| EP | 1 168 483 | 1/2002 |
| EP | 1 416 291 | 5/2004 |
| EP | 1 477 823 A | 11/2004 |
| GB | 2 286 248 | 8/1995 |
| GB | 2 289 344 | 11/1995 |
| JP | 05 269108 | 10/1995 |
| JP | 07 265278 | 10/1995 |
| WO | WO 92/17793 | 10/1992 |
| WO | WO 92/17794 | 10/1992 |
| WO | WO 92/19978 | 11/1992 |
| WO | WO 92/21989 | 12/1992 |
| WO | WO 94/05022 | 3/1994 |
| WO | WO 95/34096 | 12/1995 |
| WO | WO 96/39636 | 12/1996 |
| WO | WO 96/39638 | 12/1996 |
| WO | WO 98/37438 | 8/1998 |
| WO | WO 98/54590 | 12/1998 |
| WO | WO 99/45409 | 9/1999 |
| WO | WO 99/50689 | 10/1999 |
| WO | WO 00/70356 | 11/2000 |
| WO | WO 01/85811 | 11/2001 |
| WO | WO 02/082115 A2 | 10/2002 |
| WO | WO 02/098364 | 12/2002 |
| WO | WO 03/014700 | 2/2003 |
| WO | WO 03/040761 | 5/2003 |
| WO | WO 03/096041 | 11/2003 |
| WO | WO 04/001454 A | 12/2003 |
| WO | WO 04/102596 | 11/2004 |
| WO | WO 05/059582 A1 | 6/2005 |

OTHER PUBLICATIONS

Garroway, et al., "Narcotics and Explosives Detection by 14N pure NQR", SPIE, 1993, pp. 318-327, vol. 2092, Maryland.

Hirschfeld, et al., "Short Range Remote NQR Measurements", Journal of Molecular Structure, 1980, pp. 63-77, vol. 58, The Netherlands.

Charles Wilker, "HTS Sensors for NQR Spectroscopy", vol. 1, pp. 143-146, 2004.

Anders Stensgaard, "Optimized Design of the Shielded-Loop Resonator", Journal of Magnetic Resonance, 122, 120-126 (1996), Article No. 0187.

He, D.F. et al., "Metal detector based on high-Tc RF SQUID", Physica C 378-381 (2002) pp. 1404-1407.

Miller, et al., "Performance of a High-Temperature Superconducting Probe for In Vivo Microscopy at 2.0 T", Magnetic Resonance in Medicine, (1999), pp. 72-79, vol. 41.

W.H. Wong, et al., "HTS Coils for High Resolution Nuclear Magnetic Resonance Spectroscopy", Advances in Cryogenic Engineering, (1996), pp. 953-959, New York.

V. Kotsubo et al., "Cryogenic System for a High Temperature Superconductor NMR Probe", Advances in Cryogenic Engineering, Jul. 17, 1995, vol. 41, pp. 1857-1864, New York.

Kushida, et al., "Dependence on the Pure Quadrupole Resonance Frequency on Pressure and Temperature", Physical Review, (Dec. 1956), pp. 1364-1377, vol. 104, No. 5, Massachusetts.

Vanier, "Temperature Dependence of the Pure Nuclear Quadrupole Resonance Frequency in KC103", Canadian Journal of Physics, (Nov. 1960), pp. 1397-1405, vol. 38, No. 11, Canada.

Smith, et al., "Nitrogen Electric Quadrupole and Proton Magnetic Resonances in Thiourea", Journal of Chemical Physics, (Oct. 1964), pp. 2403-2416, vol. 41, No. 8, New York.

Turner, C. W., High temperature superconductor circuit components for cryogenic microwave systems, Electrical and Computer Engineering, 1993, Canadian Conference on Vancouver, BC Canada (Sep. 14-17, 1993) XP 010118071.

W. A. Edelstein et al., A signal-to-noise calibration procedure for NMR imaging systems, Medical Physics, vol. 11 (2) Mar./Apr. 1984, pp. 180-185.

Bendall, et al., "Elimination of Coupling between Cylindrical Transmit Coils and Surface-Receive Coils for in Vivo NMR" Magnetic Resonance in Medicine v3, pp. 157-163, 1986.

Black, et al., "A High-Temperature Superconducting Receiver For Nuclear Magnetic Resonance Microscopy", Science, vol. 259, pp. 793-795, Feb. 5, 1993.

Black, et al., "Performance Of A High-Temperature Superconducting Resonator For High-Field Imaging", Journal Of Magnetic Resonance, pp. 74-80, (1995).

Colton, et al., "Making the World a Safer Place", Science, v. 299, i. 5611, pp. 1324-1325, Feb. 2006.

Fisher, et al., "A Versatile Computer-Controlled Pulsed Nuclear Quadrupole Resonance Spectrometer", Review of Scientific Instruments, v. 70, No. 12, p. 4678, Dec. 1999.

Hill, "Improved Sensitivity of NMR Spectroscopy Probes By Use Of High-Temperature Superconductive Detection Coils", IEEE Transactions On Applied Superconductivity, vol. 7, pp. 3750-3753, Jun. 1997.

Roemer, et al., "The NMR Phased Array", Magnetic Resonance in Medicine 16, pp. 192-225, 1990.

Withers, et al., "Thin-Film HTD Probe Coils For Magnetic-Resonance Imaging", IEEE Transactions On Applied Superconductivity, vol. 3, pp. 2450-2453, Mar. 1993.

Landers, et al., "Electronic Effects and Molecular Motion in β-Octahydro-1,3,5,7-tetranitro-1,3,5,7-tetrazocine Bases on $^{14}$N Nuclear Quadrupole Resonance Spectroscopy", American Chemical Society, J. Phys. Chem., 85, pp. 2618-2623, 1961.

Karpowicz, et. Al., "Librational Motion of Hexahydro-1,3,5-trinitro-s-triazine Based on the Temperature Dependence of the Nitrogen-14 Nuclear Quadrupole Resonance Spectra: The Relationship to Condensed-Phase Thermal Decomposition", American Chemical Society, J. Phys. Chem. 87, pp. 2109-2112, 1983.

Volpicelli, et al., "Locked rf Spectrometer for Nuclear Quadrupole Resonance", The Review of Scientific Instruments, v.25, No. 2, pp. 150-153, Feb. 1965.

Benedek, et al., "Precise Nuclear Resonance Thermometer", The Review of Scientific Instruments, v. 28, No. 2, pp. 92-95, Feb. 1957.

Ernst, "Magnetic Resonance with Stochastic Excitation", Journal of Magnetic Resonance 3, pp. 10-27, 1970.

Klainer, et al., "Fourier Transform Nuclear Quadrupole Resonance Spectroscopy", Fourier, Hadamard, and Hilbert Transforms in Chemistry, pp. 147-182, 1982.

* cited by examiner

Q-DAMPING CIRCUIT INCLUDING A HIGH TEMPERATURE SUPERCONDUCTOR COIL FOR DAMPING A HIGH TEMPERATURE SUPERCONDUCTOR SELF-RESONANT COIL IN A NUCLEAR QUADRUPOLE RESONANCE DETECTION SYSTEM

This application claims the benefit of U.S. Provisional Application No. 60/524,578, filed Nov. 24, 2003, which is incorporated in its entirety as a part hereof for all purposes.

FIELD OF THE INVENTION

This invention relates to a nuclear quadrupole resonance detection system and the use of a high temperature superconductor single loop or coil in the Q-damping circuit for a high temperature superconductor transmit, receive, or transmit and receive self-resonant coil.

BACKGROUND OF THE INVENTION

The use of nuclear quadrupole resonance (NQR) as a means of detecting explosives and other contraband has been recognized for some time—see e.g. T. Hirshfield et al, *J. Molec. Struct.* 58, 63 (1980); A. N. Garroway et al, *Proc. SPIE* 2092, 318 (1993); and A. N. Garroway et al, *IEEE Trans. on Geoscience and Remote Sensing,* 39, pp. 1108-1118 (2001). NQR provides some distinct advantages over other detection methods. NQR requires no external magnet such as required by nuclear magnetic resonance. NQR is sensitive to the compounds of interest, i.e., there is a specificity of the NQR frequencies.

One technique for measuring NQR in a sample is to place the sample within a solenoid coil that surrounds the sample. The coil provides a radio frequency (RF) magnetic field that excites the quadrupole nuclei in the sample and results in their producing their characteristic resonance signals. This is the typical apparatus configuration that might be used for scanning mail, baggage or luggage. There is also need for a NQR detector that permits detection of NQR signals from a source outside the detector, e.g., a wand detector, that could be passed over persons or containers as is done with existing metal detectors. Problems associated with such a detector using conventional systems are the decrease in detectability with distance from the detector coil, and the associated equipment needed to operate the system.

The NQR detection system can have one or more coils that both transmit and receive, or it can have coils that solely transmit or solely receive. The transmit, or transmit and receive, coil of the NQR detection system provides a radio frequency (RF) magnetic field that excites the quadrupole nuclei in the sample and results in their producing their characteristic resonance signals that the receive, or transmit and receive, coil detects. The NQR signals have low intensity and short duration.

The transmit, receive, or transmit and receive, coil is preferably tunable and has a high quality factor (Q). After the RF signal is transmitted, the transmit, receive, or transmit and receive, coil will typically experience ringing, and it must have a rapid recovery time in order for the receive, or transmit and receive, coil to be able to detect the low intensity NQR signal. One method of accomplishing this is to use a Q-damping circuit that is activated to provide a rapid recovery.

A simple Q-damping circuit is shown in FIG. 1. The transmit, receive or transmit and receive, coil 1 is inductively coupled to single loop or coil 2. The Q-damping circuit is comprised of single loop or coil 2, a diode switch 3, a capacitor 4 and a resistor 5. Various other component arrangements can be used between points 6 and 7, such as those shown in Kim, U.S. Pat. No. 6,291,994. The single loop or coil 2 can be a single loop, a solenoid, or a center-taped single loop or solenoid. The diode switch 3 is open when no damping is needed and closed, so that the resistive load can provide the Q-damping, when damping is needed.

The transmit, receive, or transmit and receive, coil has typically been made of copper and therefore has a Q of about $10^2$. It is advantageous to use a transmit, receive, or transmit and receive, coil made of a high temperature superconductor (HTS) rather than copper since the HTS self-resonant coil has a Q of the order of $10^3$-$10^6$. The recovery time is proportional to Q so that a HTS coil has a considerably longer recovery time than a copper coil, and the presence of a Q-damping circuit is especially important. One difficulty encountered when using a HTS self-resonant coil and a copper single loop or coil in the Q-damping circuit is that the very high Q of the HTS coil can be degraded by the eddy currents in the copper single loop or coil.

An object of the present invention is to reduce the eddy current losses in the single loop or coil in the Q-damping circuit and thereby essentially eliminate the degradation in Q of the HTS coil.

SUMMARY OF THE INVENTION

This invention provides a nuclear quadrupole resonance detection system that includes a high temperature superconductor self-resonant transmit, receive, or transmit and receive, coil; and a Q-damping circuit for the transmit, receive, or transmit and receive, coil; wherein the Q-damping circuit includes a high temperature superconductor single loop or coil. Preferably, the high temperature superconductor single loop or coil of the Q-damping circuit is inductively coupled to the high temperature superconductor self-resonant transmit, receive or transmit and receive, coil. Preferably, the inductively coupled Q-damping circuit includes a high temperature superconductor single loop.

Preferably, the high temperature superconductor self-resonant transmit, receive, or transmit and receive, coil is a planar or surface coil.

This detection system is especially useful for detecting explosives, drugs and other contraband.

DETAILED DESCRIPTION OF THE PREFERRED EMBODIMENTS

Figure 1:
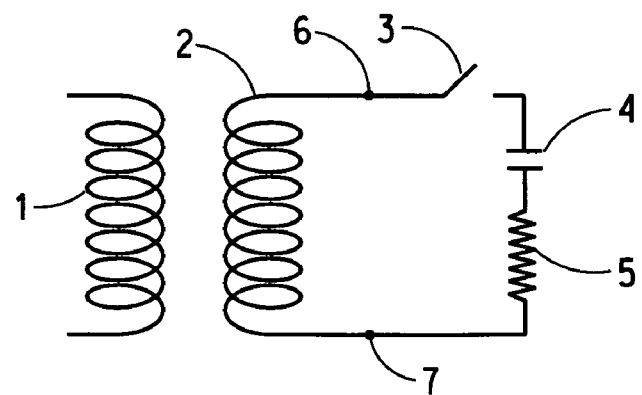
FIG. 1 shows a simple Q-damping circuit of the prior art.

This invention relates to a NQR detection system comprising a high temperature superconductor self-resonant transmit, receive, or transmit and receive, coil and a Q-damping circuit containing a high temperature superconductor single loop or coil. For some applications, it is advantageous to have separate transmit and receive coils. In these instances, one or both of the coils can be HTS self-resonant coils. For some detection purposes, the NQR detection system will be comprised of a single transmit and receive coil or a single set of separate transmit and receive coils. For other detection purposes, the NQR detection system will be comprised of two or more transmit and receive coils or two or more sets of separate transmit and receive coils. In these instances, there will be a Q-damping circuit for at least one of the HTS coils and preferably for all of the HTS coils.

The HTS single loop or coil in the Q-damping circuit greatly reduces the eddy current losses that would be present with a copper single loop or coil, and essentially eliminates the Q degradation of the HTS transmit, receive, or transmit and receive, coil that results from such losses when copper is used.

The planar or surface coil preferred for use as the high temperature superconductor self-resonant transmit, receive, or transmit and receive, coil in this invention has a HTS coil configuration on only one side of the substrate, or has essentially identical HTS coil configurations on both sides of the substrate.

It is often advantageous to be able to fine tune the resonance frequency. One means for accomplishing such tuning is to use two coupled high temperature superconductor self-resonant planar coils. The resonance frequency of the fundamental symmetric mode of the two coupled high temperature superconductor self-resonant planar coils can be varied by mechanically displacing one coil with respect to the other, and these coupled coils serve as the HTS transmit, receive or transmit and receive coil.

Preferably, the HTS single loop or coil in the Q-damping circuit is a single loop of HTS on a substrate. Preferably, the HTS self-resonant transmit, receive, or transmit and receive, coil and the HTS single loop in the Q-damping circuit are on the same substrate.

The use of a HTS self-resonant planar transmit, receive, or transmit and receive, coil provides several advantages over the conventionally-used copper coil. These advantages arise from the high Q of the HTS self-resonant coil, which has Q's on the order of $10^3$-$10^6$ compared to the typical Q of $10^2$ for a copper system. The large Q of the HTS self-resonant coil produces large magnetic field strengths during the RF transmit pulse and does so at lower RF power levels. This dramatically reduces the amount of transmitted power required to produce NQR signals for detection and thereby reduces the size of the RF power supply sufficiently so that it can be run on portable batteries. The large Q of the HTS self-resonant coil also plays an important role during the receive time. As the signal-to-noise (S/N) ratio is proportional to the square root of Q, the use of the HTS self-resonant coil results in an increase in S/N by a factor of 10-100 over that of the copper system. These advantages during both the transmit and the receive times enable a detector configuration that is small and portable. It is therefore important to be able to introduce Q-damping without Q-degradation due to eddy currents in the Q-damping circuit single loop or coil.

The high temperature superconductors used to form the HTS self-resonant coil, and the single loop or coil in the Q-damping circuit, are preferably selected from the group consisting of $YBa_2Cu_3O_7$, $Tl_2Ba_2CaCu_2O_8$, $TlBa_2Ca_2Cu_3O_9$, $(TlPb)Sr_2CaCu_2O_7$ and $(TlPb)Sr_2Ca_2Cu_3O_9$. Most preferably, the high temperature superconductor is $YBa_2Cu_3O_7$ or $Tl_2Ba_2CaCu_2O_8$.

The HTS self-resonant coil and HTS Q-damping circuit single loop or coil can be formed by various known techniques. Preferably, a planar coil is formed by first depositing HTS layers on both sides of a single crystal substrate. A single loop can be formed on one or both sides of the substrate. In a preferred technique, the HTS layers are formed directly on a single crystal $LaAlO_3$ substrate, or on a $CeO_2$ buffer layer on a single crystal sapphire ($Al_2O_3$) substrate.

When the high temperature superconductor is $Tl_2Ba_2CaCu_2O_8$, an amorphous precursor layer of Ba:Ca:Cu oxide about 500 nm thick and with a stoichiometry of about 2:1:2 is deposited by off-axis magnetron sputtering from a Ba:Ca:Cu oxide target. The precursor film is then thallinated by annealing it in air for about 45 minutes at 850° C. in the presence of a powder mixture of $Tl_2Ba_2Ca_2Cu_3O_{10}$ and $Tl_2O_3$. When this powder mixture is heated, $Tl_2O$ evolves from the powder mixture, diffuses to the precursor film and reacts with it to form the $Tl_2Ba_2CaCu_2O_6$ phase.

The sample is then coated with photoresist on both sides and baked. A coil design mask or a single loop design mask is prepared. The design mask is then centered on the photoresist covering the $Tl_2Ba_2CaCu_2O_8$ film on the front side of the substrate and exposed to ultraviolet light. If the coil or single loop is to have the same HTS pattern on both sides of the substrate, the design mask is then centered on the photoresist covering the $Tl_2Ba_2CaCu_2O_8$ film on the back side of the substrate and exposed to ultraviolet light. The resist is then developed on both sides of the substrate, and the portion of the $Tl_2Ba_2CaCu_2O_8$ film exposed when the resist is developed is etched away by argon beam etching. The remaining photoresist layer is then removed by an oxygen plasma. The result is the desired HTS coil or single loop.

Figure 2:
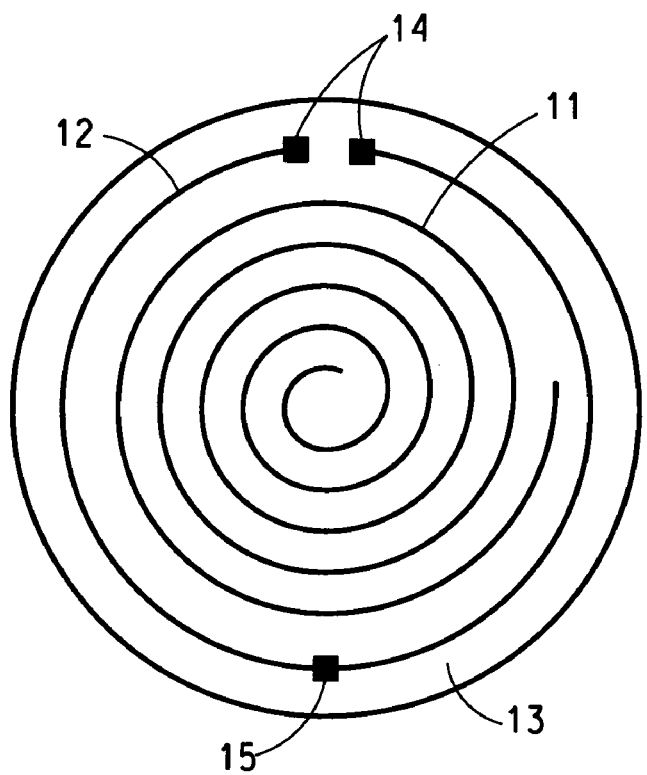
FIG. 2 is a depiction of an embodiment of the invention in which the HTS transmit, receive, or transmit and receive, coil and the HTS single loop of the Q-damping circuit are on the same substrate.

One embodiment of the invention is depicted in FIG. 2. An HTS self-resonant transmit, receive, or transmit and receive, coil 11 and an HTS single loop 12 are shown on circular substrate 13. Gold pads 14 at each end of the HTS single loop 12 serve as means to connect the HTS single loop 12 to the remainder of the Q-damping circuit, which is not shown in FIG. 2. Connectors from gold pads 14 would connect to points 6 and 7 shown in FIG. 1. An optional gold pad 15 is shown in FIG. 2 to provide a center-taped single loop.

When a copper, silver or aluminum coil is used as the transmit coil, it is preferably in the form of a shielded-loop resonator (SLR) coil. SLR's have been developed to eliminate the detuning effect of the electrical interaction between the coil and the surrounding material.

Provision must be made for a power supply to supply power for transmitting the RF pulse as well as provision for related circuitry for processing the detected NQR signal. Provision must also be made for cooling the HTS coil to at least liquid nitrogen temperature.

Where an apparatus of this invention is stated or described as comprising, including, containing, having, being composed of or being constituted by certain components, it is to be understood, unless the statement or description explicitly provides to the contrary, that one or more components other than those explicitly stated or described may be present in the apparatus. In an alternative embodiment, however, the apparatus of this invention may be stated or described as consisting essentially of certain components, in which embodiment components that would materially alter the principle of operation or the distinguishing characteristics of the apparatus would not be present therein. In a further alternative embodiment, the apparatus of this invention may be stated or described as consisting of certain components, in which embodiment components other than those as stated would not be present therein.

Where the indefinite article "a" or "an" is used with respect to a statement or description of the presence of a component in an apparatus of this invention, it is to be understood, unless the statement or description explicitly provides to the contrary, that the use of such indefinite article does not limit the presence of the component in the apparatus to one in number.

What is claimed is:

1. A nuclear quadrupole resonance detection system comprising a high temperature superconductor self-resonant receive coil and a high temperature superconductor self-resonant transmit coil,
    a first Q-damping circuit for the receive coil and a second Q-damping circuit for the transmit coil,
    wherein the first and second Q-damping circuits each comprise a high temperature superconductor single loop or coil.

2. The nuclear quadrupole resonance detection system of claim 1, wherein the high temperature superconductor single loop or coil of the second Q-damping circuit is inductively coupled to the high temperature superconductor self-resonant transmit coil.

3. The nuclear quadrupole resonance detection system of claim 1, wherein the high temperature superconductor self-resonant receive coil is a planar coil, and each high temperature superconductor single loop or coil is a single loop on a substrate.

4. The nuclear quadrupole resonance detection system of claim 3, wherein the high temperature superconductor self-resonant receive coil and the high temperature superconductor single loop associated therewith are on the same substrate.

5. A nuclear quadrupole resonance detection system comprising
    a high temperature superconductor self-resonant receive coil and a high temperature superconductor self-resonant transmit coil,
    a first Q-damping circuit for the receive coil and a second Q-damping circuit for the transmit coil,
    wherein the first and second Q-damping circuits each comprise a high temperature superconductor single loop or coil, and
    wherein the high temperature superconductor single loop or coil of the first Q-damping circuit is inductively coupled to the high temperature superconductor self-resonant receive coil.

6. The nuclear quadrupole resonance detection system of claim 5, wherein the high temperature superconductor single loop or coil of the second Q-damping circuit for the receive coil is inductively coupled to the transmit coil.

7. The nuclear quadrupole resonance detection system of claim 5, wherein the high temperature superconductor self-resonant receive coil is a planar coil, and each high temperature superconductor single loop or coil is a single loop on a substrate.

8. The nuclear quadrupole resonance detection system of claim 7, wherein the high temperature superconductor self-resonant receive coil and the high temperature superconductor single loop associated therewith are on the same substrate.

* * * * *